US012766240B2

(12) United States Patent
Gliner et al.

(10) Patent No.: US 12,766,240 B2
(45) Date of Patent: Oct. 20, 2026

(54) ANTI-VACUUM SURGE MODULE WITH POWER AND DATA TRANSMISSION COILS

(71) Applicant: JOHNSON & JOHNSON SURGICAL VISION, INC., Irvine, CA (US)

(72) Inventors: Vadim Gliner, Haifa (IL); Assaf Govari, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 528 days.

(21) Appl. No.: 18/116,211

(22) Filed: Mar. 1, 2023

(65) Prior Publication Data

US 2023/0364320 A1 Nov. 16, 2023

Related U.S. Application Data

(60) Provisional application No. 63/340,594, filed on May 11, 2022.

(51) Int. Cl.

*A61M 1/00* (2006.01)
*A61F 9/007* (2006.01)
*A61M 39/10* (2006.01)

(52) U.S. Cl.

CPC ........... *A61M 1/86* (2021.05); *A61F 9/00745* (2013.01); *A61M 1/77* (2021.05); *A61B 2217/005* (2013.01); *A61B 2217/007* (2013.01); *A61M 2039/1022* (2013.01); *A61M 2205/3341* (2013.01)

(58) Field of Classification Search

CPC ........ A61M 1/77; A61M 1/86; A61F 9/00745
See application file for complete search history.

(56) References Cited

U.S. PATENT DOCUMENTS

| | | | | | |
|---|---|---|---|---|---|
| 2009/0048607 | A1* | 2/2009 | Rockley | A61M 1/77 | 606/107 |
| 2010/0185150 | A1 | 7/2010 | Zacharias | | |
| 2014/0323953 | A1* | 10/2014 | Sorensen | A61F 9/00745 | 604/35 |
| 2016/0094051 | A1* | 3/2016 | Soar | H02J 50/70 | 307/9.1 |
| 2020/0289319 | A1 | 9/2020 | Carter et al. | | |
| 2020/0353133 | A1 | 11/2020 | Gao et al. | | |
| 2020/0383833 | A1 | 12/2020 | Schaller | | |

(Continued)

FOREIGN PATENT DOCUMENTS

EP 2305143 A1 4/2011

OTHER PUBLICATIONS

U.S. Appl. No. 17/511,166, Anti-Vacuum Surge System, filed Oct. 26, 2021.

(Continued)

*Primary Examiner* — Erin Mcgrath

(57) ABSTRACT

Methods and systems provide provides a vacuum surge protection system or an Anti-Vacuum Surge (AVS) module and a console-side connector that form an energy (power) and/or data transfer system, which passes the energy and/or data using a magnetic field, via non-contact magnetic induction, between the console-side connector and the AVS module. The AVS module typically powers a medical tool, such as a phacoemulsification handpiece, for ophthalmic procedures, such as cataract removal.

20 Claims, 6 Drawing Sheets

(56) References Cited

U.S. PATENT DOCUMENTS

2022/0133537 A1 5/2022 Govari et al.

OTHER PUBLICATIONS

Khan, Sadeque Reza et al. "Wireless Power Transfer Techniques for Implantable Medical Devices: A Review." Sensors (Basel, Switzerland) vol. 20,12 3487. Jun. 19, 2020, doi:10.3390/s20123487.

DN Staff, "Understanding non-contact transmission of power and sensor signals", https://www.designnews.com/understanding-non-contact-transmission-power-and-sensor-signals; Jun. 1, 2001.

* cited by examiner

ANTI-VACUUM SURGE MODULE WITH POWER AND DATA TRANSMISSION COILS

CROSS-REFERENCE TO RELATED APPLICATIONS

This application claims the benefit of U.S. Provisional Patent Application 63/340,594, filed May 11, 2022, whose disclosure is incorporated herein by reference.

TECHNICAL FIELD

The present disclosure relates generally to connector modules for phacoemulsification handles or hand pieces, and particularly to methods and systems for power and data transfer to the connector module.

BACKGROUND

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece, also known as a handle, with a needle. The tip of the needle vibrates at ultrasonic frequency to sculpt and emulsify the cataract while a pump aspirates particles and fluid from the eye through the tip. Aspirated fluids are replaced with irrigation of a balanced salt solution (BSS) to maintain the anterior chamber of the eye. After removing the cataract with phacoemulsification, the softer outer lens cortex is removed with suction. An intraocular lens (IOL) is then introduced into the empty lens capsule restoring the patient's vision.

The handpiece is provided its power from a connector module, that communicates with a console. The connector module connects electrically to the handpiece, through multiple individual module connections. Through these multiple individual module connections, power and data are transferred, to operate the connector module and the handpiece.

BRIEF DESCRIPTION OF THE DRAWINGS

The present disclosure will be more fully understood from the following detailed description of examples thereof, taken together with the drawings, where like numerals or characters indicate corresponding or like components, in which.

DETAILED DESCRIPTION OF EXAMPLES

Overview

Figure 1:
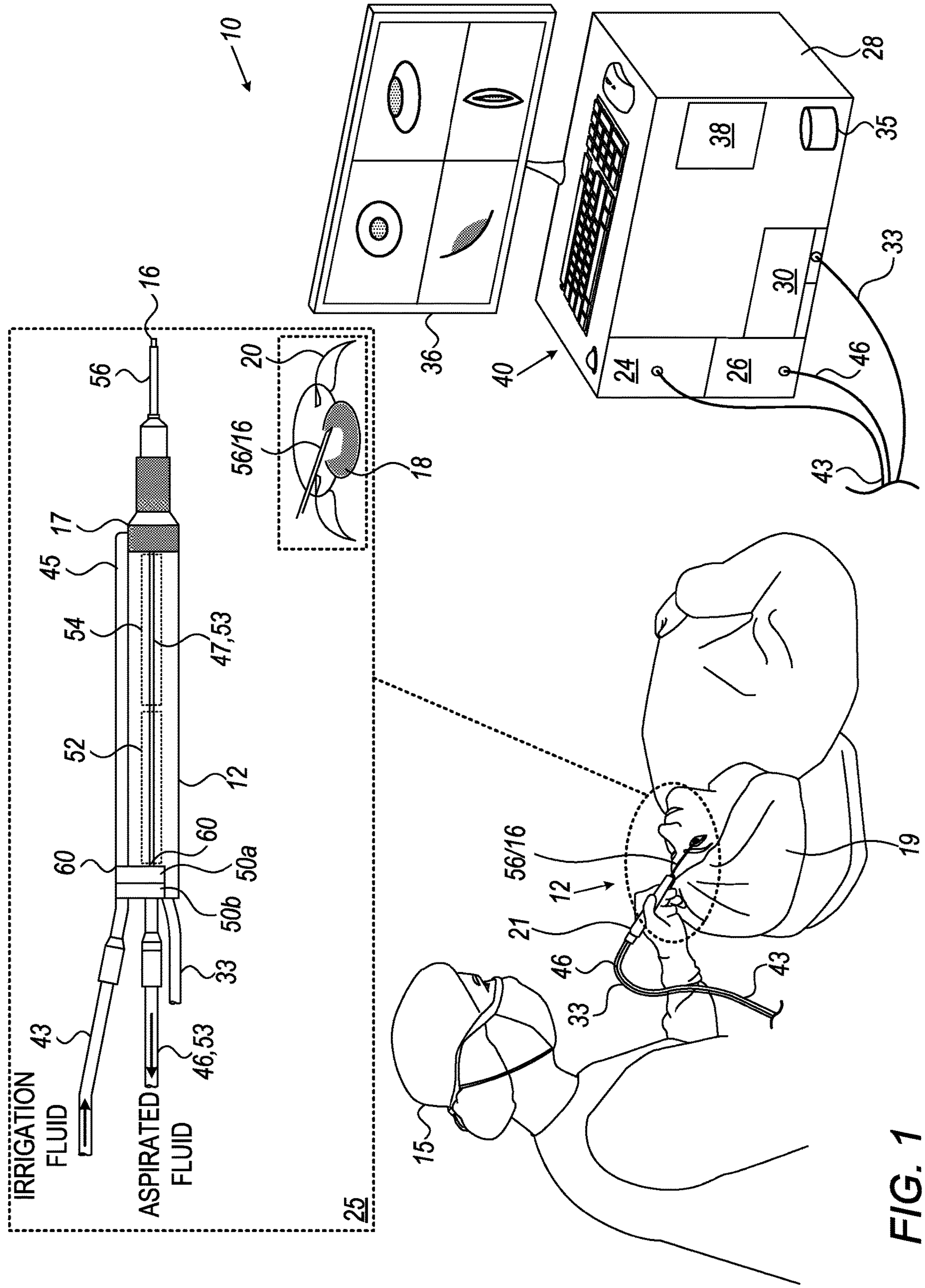
FIG. 1 is a block diagram that schematically illustrates an example phacoemulsification system, in accordance with an example of the present disclosure.

During phacoemulsification of an eye lens, the emulsified lens particles are aspirated. When a particle blocks the inlet of an aspiration channel (which could be a needle of a phacoemulsification probe) causing occlusion of the channel, the vacuum in the channel increases. When the channel becomes unblocked (e.g., by the particle being subsequently sucked down the channel), the build-up of vacuum in the channel causes an aspiration surge known as a post occlusion surge, which may have traumatic consequences to the eye. For example, sensitive parts of the eye may be damaged or come into contact with the needle of the phacoemulsification probe.

An Anti-Vacuum Surge (AVS) System, such as that disclosed, for example, in commonly owned U.S. patent application Ser. No. 17/511,166, title: Anti-Vacuum Surge System, filed on Oct. 26, 2021, the disclosure of which is incorporated by reference herein, functions to remove or reduce the pressure difference in the aspiration channel during the occlusion clearance. The AVS system includes an AVS connector module, also referred to herein as an AVS module (for connecting to a handpiece) and a console-side connector. The AVS connector module includes a valve, e.g., a fast-acting and programmable solenoid valve, which restricts or otherwise blocks fluid connectivity in the aspiration channel during occlusion clearance based on detection of a change in pressure, e.g., sharp or quick change, in the aspiration channel. The vacuum can then be reduced in a controlled manner until an acceptable pressure is achieved, allowing the valve to be opened again. The solenoid valve, for example, includes a solenoid coil, which moves a plunger, that includes a permanent magnet in a valve cavity.

The AVS system is generally constantly operational, and the valve closes on detection of a change in pressure, even if the phacoemulsification needle is not being vibrated and there is a low risk associated with the needle damaging the eye.

The AVS system activates the valve, for example, according to a pressure change (e.g., rate of change in pressure or other fluid metric) in the aspiration channel, during a time period when the needle is being vibrated, to close off the aspiration channel, where vacuum was increasing, due to an occlusion or decreasing, due to an occlusion break. As a result, pressure in the aspiration line can be adjusted prior to the valve opening to prevent post occlusion surge. If there is no particle at the tip and the phacoemulsification probe needle is not vibrated, then the pump continues to run to bring particles to the tip.

The disclosed system provides an AVS module and a console-side connector that form an energy (power) and/or data transfer system, which passes the energy and/or data using a magnetic field, via non-contact magnetic induction. The magnetic induction is formed, for example, between magnetic coils, at least one coil in the AVS module and at least one coil in the console-side connector, separated (divided) by a separator, which is, for example, an insulating separator. A thin insulating separator, for example, at least on one of the AVS module or the console-side connector, enables the coils to be close together, while providing electrical insulation.

This arrangement of the magnetic coils, separated by the insulating separator eliminates the use of electrical connections between the AVS module and the handpiece. Accordingly, many, and typically all of, the individual electrical and data connections, in the AVS module are eliminated, as the electrical and data signals are transferred/transmitted via single coils on the AVS module and a mating console-side connector. This arrangement of coils also allows for transmission of electricity and/or data to proceed as normal, even when the coils are misaligned, avoiding interrupted electrical and data transmission. Also, since the coils use magnetic connections, transmission problems which may arise from moisture contacting dedicated electrical connections in the AVS module and the handpiece are eliminated. In some examples, a single pair of coils is used for transferring an electrical power signal modulated with data, but more than a single pair of coils are also envisioned.

The AVS module coil can, for example, be used to power the AVS module, and also provide power to operate the handpiece, through the AVS module. In addition, the AVS module coil may be used to charge a capacitor in the AVS module, that may be used if additional electrical energy is required, for example, to power the solenoid coil of the solenoid valve, which moves between open and closed states. In the closed state, the aspiration line or channel is closed by the solenoid valve, to prevent a vacuum surge, and the solenoid valve is then moved to the open state, opening the aspiration line or channel, when the vacuum surge or vacuum build-up is reduced, no longer present or is not present.

The disclosed system provides a console-side connector, that connects with the AVS module, so that the AVS module and handpiece operate to perform a phacoemulsification process. The console-side connector and the AVS module each include at least one magnetic coil, with the coil in the console-side connector coupled and communicating with the coil in the AVS module, to pass magnetic energy between the coils. The magnetic induction, e.g., the passage of magnetic energy between the coils, provides for power (e.g., energy, including electricity) and/or data transfer between the connector and the AVS module, the transferred power for operating the AVS module and the handpiece (e.g., via the AVS module).

In some examples, the coupled magnetic coils of the console-side connector and the AVS module provide a power scheme that alternates between providing pulses of power for charging a capacitor and activating the AVS with pulses. By using short pulses delivered over a fraction of a millisecond, the threshold of power typically defined over 1 millisecond (msec) may be exceeded. The short pulses charge the capacitor. The stored energy in the capacitor may be released to instantaneously power the solenoid valve, to immediately close the aspiration line, in response to a vacuum surge being detected in the aspiration line (for example, by a sensor in the AVS module).

System Description

Reference is now made to FIG. 1, that is a partly pictorial, partly block diagram view of a phacoemulsification system 10 constructed and operative in accordance with an example of the present disclosure.

The phacoemulsification system 10 comprises a phacoemulsification probe 12, also known as a handle or handpiece, these terms used interchangeably herein. In some examples, the phacoemulsification probe 12 may be replaced by any suitable medical tool. As seen in the pictorial view of phacoemulsification system 10, and in inset 25, the phacoemulsification probe 12 comprises a needle 16, a probe body 17, and a coaxial irrigation sleeve 56 that at least partially surrounds needle 16 and creates a fluid pathway between the external wall of the needle and the internal wall of the irrigation sleeve, where needle 16 is hollow to provide an aspiration channel. Moreover, irrigation sleeve 56 may have one or more side ports at, or near, the distal end to allow irrigation fluid to flow towards the distal end of the phacoemulsification probe 12 through the fluid pathway and out of the port(s).

The needle 16 of the phacoemulsification probe 12 is configured for insertion into a lens capsule 18 of an eye 20 of a patient 19 by a physician 15 to remove a cataract. While the needle 16 (and irrigation sleeve 56) are shown in inset 25 as a straight object, any suitable needle may be used with phacoemulsification probe 12, for example, a curved or bent tip needle commercially available from Johnson & Johnson Surgical Vision, Inc., Santa Ana, CA, USA.

In the example of FIG. 1, during the phacoemulsification procedure, a pumping sub-system 24 comprised in a console 28 pumps irrigation fluid from an irrigation reservoir (not shown) to the irrigation sleeve 56 to irrigate the eye 20. The irrigation fluid is pumped via an irrigation tubing line 43 running from the console 28 to an irrigation channel 45 of probe 12, the distal end of the irrigation channel 45 including the fluid pathway in the irrigation sleeve 56. The irrigation tubing line 43 is typically flexible and may be prone to collapsing during an occlusion of the needle 16. In another example, the pumping sub-system 24 may be coupled or replaced with a gravity fed irrigation source such as a BSS (balanced salt solution) bottle/bag.

Eye fluid and waste matter (e.g., emulsified parts of the cataract) are aspirated via an aspiration channel 47, which extends from the hollow of needle 16 through the phacoemulsification probe 12, and then via an aspiration tubing line 46 to a collection receptacle (not shown) coupled with the console 28. The aspiration is affected by a pumping sub-system 26, also comprised in console 28. The aspiration tubing line 46 and the aspiration channel 47 are described herein as an aspiration line 53. The aspiration line 53 is therefore partially disposed in the needle 16 and is connected to the pumping sub-system 26, which is configured to remove the fluid and waste matter from the eye 20 via the aspiration line 53.

The system 10 includes an AVS module 50*a*, for example, in the form of a cartridge (which in an example, may be removable), which mates (couples) with and is in magnetic induction with a console-side connector 50*b* and couples with the distal end of the probe body 17. The magnetic induction is between coils, at least one coil, and typically a single coil, in each of the AVS module 50*a* and console-side connector 50*b*, e.g., coils 100, 101 (FIGS. 3A, 3B, 4 and 5). Through the magnetic induction between the coils 100, 101, energy (e.g., power) and/or data are transferred and transmitted between the coils 100, 101. The coils 100, 101, for example, carry current, such as alternating current (AC), which when flowing through the coils 100, 101, via magnetic induction, creates a magnetic field, allowing for the transfer of energy and/or data to the AVS module 50*a*, which in turn, transfers energy and/or data to the probe 12.

The AVS module 50*a*, includes, for example, a vacuum surge protection system 51 (see FIGS. 3A, 3B, and 4), which includes, for example, one or more valves, optionally along the irrigation channel 45 to regulate the flow of fluid in the irrigation channel 45, and a valve 64 along the aspiration channel 47, to regulate the vacuum therein. There are also sensors 68, 70, described in more detail with reference to FIGS. 3A, 3B, and 4, and a controller 74, which communicates with the sensors 68, 70 and the one or more valves, including the valve 64 along the aspiration channel 47, to signal the one or more valves to open and close the irrigation channel 45 and/or aspiration channel 47. For example, with respect to a valve 64 coupled with the aspiration channel 47, the controller 74 may signal the valve 64 to open or close depending on the pressure detected by sensor 70 in the aspiration channel 47. Part of the irrigation channel 45 and the aspiration channel 47 is disposed in the probe body 17 and part is disposed in the AVS module 50*a* and the console-side connector 50*b*.

Phacoemulsification probe 12 includes other elements, such as an ultrasonic actuator 52, e.g., piezoelectric crystal (s), coupled with a horn 54 configured to support the needle 16 and drive vibration of needle 16 to emulsify the lens of the eye 20. The ultrasonic actuator 52 is configured to vibrate the needle 16 in a resonant vibration mode. The vibration of the needle 16 is used to break a cataract into small pieces during a phacoemulsification procedure. Console 28 comprises an ultrasonic (e.g., piezoelectric) drive module 30, coupled with the ultrasonic actuator 52, using electrical wiring running in a cable 33. Drive module 30 is controlled by a controller 38 and conveys processor-controlled driving signals via cable 33 to, for example, maintain needle 16 at maximal vibration amplitude. The drive module may be realized in hardware or software, for example, in a proportional-integral-derivative (PID) control architecture. The controller 38 may also be configured to receive signals from sensors in the phacoemulsification probe 12 and control one or more valves to regulate the flow of fluid in the irrigation channel 45 and/or the aspiration channel 47. In some examples, at least some of the functionality of the controller 38 may be implemented using a controller disposed in the phacoemulsification probe 12 (e.g., the AVS module 50*a*).

Controller 38 may receive user-based commands via a user interface 40, which may include setting a vibration mode and/or frequency of the ultrasonic actuator 52 and setting or adjusting an irrigation and/or aspiration rate of the pumping sub-systems 24/26. In some examples, user interface 40 and a display 36 may be combined as a single touch screen graphical user interface. In some examples, the physician 15 uses a foot pedal (not shown) as a means of control. Additionally, or alternatively, controller 38 may receive the user-based commands from controls located in a handle 21 of probe 12.

Some or all of the functions of controller 38 may be combined in a single physical component or, alternatively, implemented using multiple physical components. These physical components may comprise hard-wired or programmable devices, or a combination of the two. In some examples, at least some of the functions of controller 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The system 10 shown in FIG. 1 may include further elements which are omitted for clarity of presentation. For example, physician 15 typically performs the procedure using a stereomicroscope or magnifying glasses, neither of which are shown. Physician 15 may use other surgical tools in addition to probe 12, which are also not shown in order to maintain clarity and simplicity of presentation.

Figure 2:
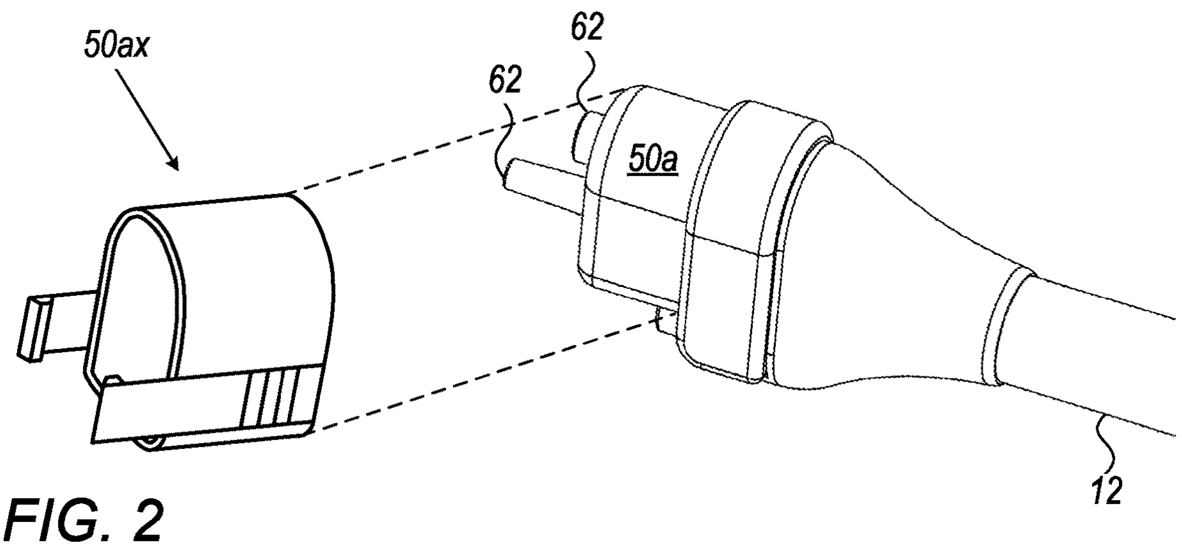
FIG. 2 is a drawing of a phacoemulsification handle or handpiece with an anti-vacuum surge (AVS) module attached thereto.

Reference is now made to FIG. 2, which shows a perspective view of the phacoemulsification probe 12 with the AVS module 50*a* engaged therein, for use with the system of FIG. 1. The cover 50*ax* of the AVS module 50*a* is shown removed from the AVS module 50*a*.

Figure 3A:
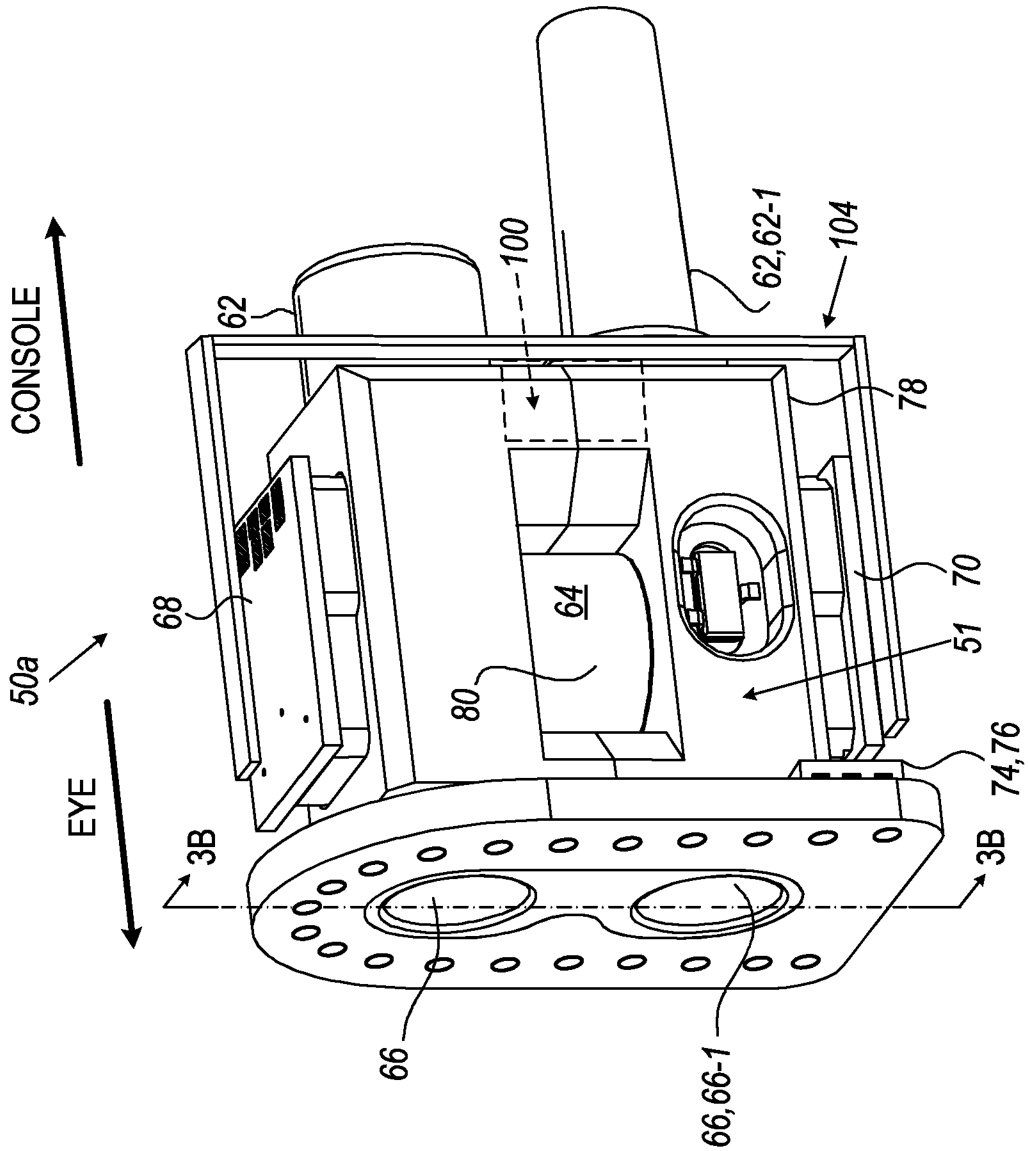
FIG. 3A is a cut away perspective view of an AVS module in accordance with an example of the present disclosure.
Figure 3B:
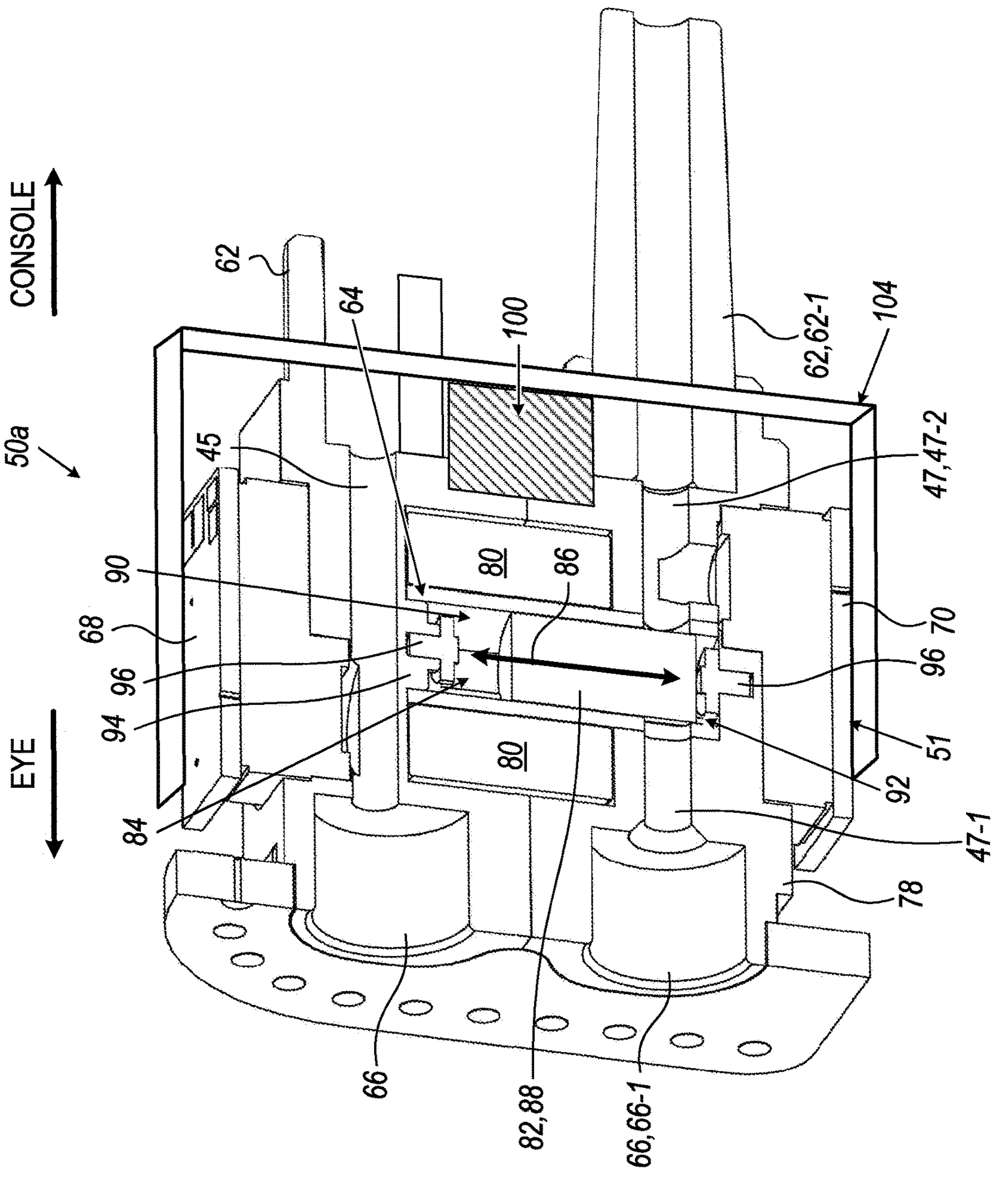
FIG. 3B is a cross-sectional view of the AVS module of FIG. 3A, taken along line 3B-3B of FIG. 3A.

FIGS. 3A and 3B show the AVS module 50*a* detached from the probe body 17. Ports 60 (FIG. 1) of the irrigation channel 45 and the aspiration channel 47 on the probe body 17 connect with corresponding ports 62 of the AVS module 50*a*. The irrigation tubing line 43 and aspiration tubing line 46 connect to ports 62 of the AVS module 50*a*.

The AVS module 50*a* typically includes, for example, a solenoid valve 64, which includes ports 62 for connection to the irrigation tubing line 43 and aspiration tubing line 46 of the console-side connector 50*b*, ports 66 for connection to the ports 60 of the handpiece 12, and sections of the irrigation channel 45 and aspiration channel 47; the sensor 68 coupled with the irrigation channel 45; and the sensor 70 coupled with aspiration channel 47 of the console-side connector 50*b*. Sensors 68, 70 are configured to provide respective signals indicative of respective fluid metrics (e.g., pressure levels) in the irrigation channel 45 and in the aspiration channel 47. The aspiration channel 47 traverses the solenoid valve 64. The sensors 68, 70 in the AVS module 50*a* typically provide higher sensitivity to local changes in fluid dynamics and provide a higher degree of control of the pressure in the eye.

Figure 4:
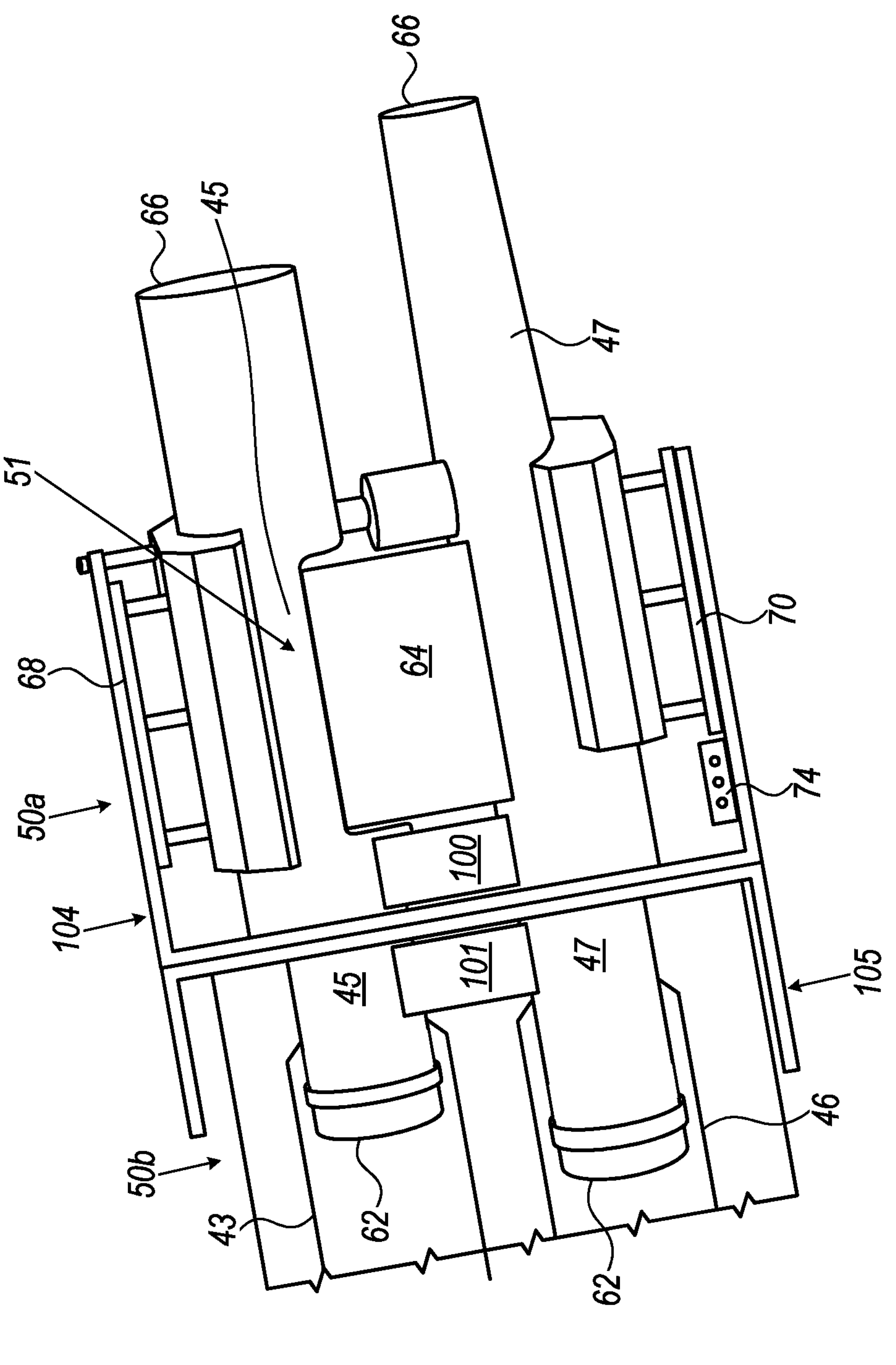
FIG. 4 is a perspective view of the AVS module mated with the console-side connector of FIG. 1.
Figure 5:
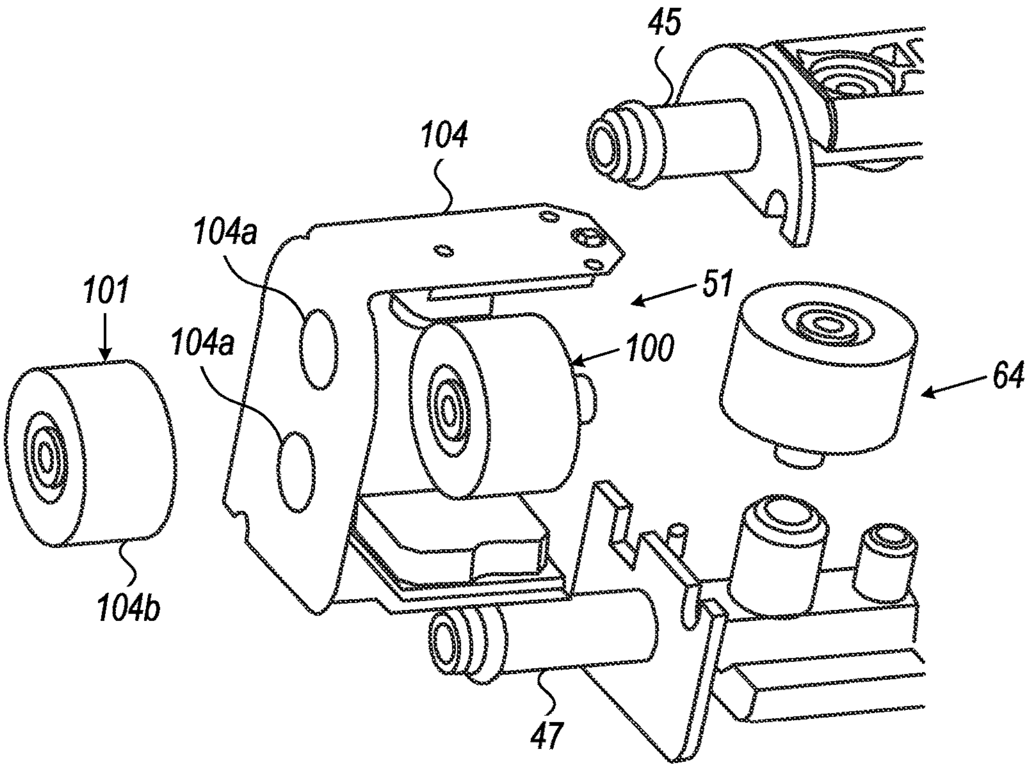
FIG. 5 is an exploded view of the AVS module and the console-side connector of FIGS. 1 and 4.

Turning to FIG. 4, there is shown a perspective view of the AVS module 50*a* in a mating connection or coupled, e.g., magnetically coupled, with the console-side connector 50*b*. FIGS. 4 and 5 show the power and data transmission system of the disclosure, for example, provided by the AVS module 50*a* and the console-side connector 50*b*.

The AVS module 50*a* includes a coil 100, in contact with, or in close proximity to, a separator 104. The separator 104, is, for example, of an electrically insulating material, such as polyvinyl chloride (PVC), and is, for example, of a thickness of approximately 0.1 mm to 3 mm. The separator 104 includes openings or apertures 104*a*, 104*b* to accommodate the irrigation 45 and aspiration 47 channels, respectively. Similarly, the console-side connector 50*b* is such that the coil 101 is at or proximate to an electrically insulating layer 105, which is typically the same material as the separator 104 and of a thickness of approximately 1 mm. In this mating connection or coupling, the coils 100, 101, are close together, to provide a non-contact magnetic connection or magnetic coupling. This magnetic connection is through which power (e.g., energy including electricity, e.g., as current) and/or data, is transferred between the coils 100, 101, free of signal degradations, interference and/or transmission interruptions. For example, the coils 100, 101 are approximately 5 mm, from each other, when the AVS module 50*a* and the console-side connector 50*b* are mated or coupled.

The coils 100,101 are such that when the AVS module 50*a* is mated or otherwise coupled or connected with the console-side connector 50*b*, as shown in FIG. 4, the coils 100, 101 are aligned. However, because coils 100, 101 are in magnetic induction, with the current transferred from the console-side coil 101 to the AVS module coil 100, the coils 100, 101 need not be in perfect alignment, and may be misaligned, for example, up to approximately 3 mm, with the magnetic induction between the coils 100, 101 remaining fully operational. The magnetic induction allows signal transmissions for transferring energy (power) and data between the coils 100, 101, for example, from console-side coil 101 to AVS module coil 100.

The coil or coils 100 in the AVS module 50*a* may be used for powering the AVS module 50*a*, supplying its electrical needs, as well as powering the handpiece 12, also supplying its electrical needs.

The coil or coils 101 in the console-side connector 50*b*, produce the magnetic energy for the power and/or data transfer and transmissions. The coil or coils 101 receive energy generated by the hardware inside the console 28.

The AVS module 50*a*, and/or the console-side connector 50*b* may include indicator light emitting diodes (LEDs) (not shown), or the like, in communication with sensors (not shown), that show if the magnetic induction between the coils 100, 101 is operating properly, such that energy and/or data is passing between the coils 100, 101 in an uninterrupted manner. For example, proper operation of the coils 100, 101 is indicated by a solid or non-blinking LED, while malfunctioning or impeded coils 100, 101 are indicated by the LEDs blinking.

Additionally, there may be other indicators, for example, LEDs in the AVS module 50*a*, and/or the console-side connector 50*b*, to indicate whether the aspiration (vacuum) 47 channel in or associated with the AVS module 50*a*, including in the console-side connector 50*b* or the handpiece 12, are clear or blocked.

Returning to FIGS. 3A and 3B, the AVS module 50*a* may include a controller 74 to receive the signal(s) from the pressure sensor 68 and/or the pressure sensor 70 and control the fluid connectivity in the irrigation channel 45 and/or the aspiration channel 47 by selectively opening and closing one or more valves 64, responsively to the received signal(s). In some examples, the AVS module 50*a* may also include the controller 74 and/or a memory 76 (e.g., EEPROM) to hold calibration settings and/or a usage counter to count usage of the AVS module 50*a* and thereby prevent overuse of the AVS module 50*a*. In some examples, the controller 74 may be included in the console 28. In some examples, the functionality of the controller 74 may be performed by the controller 38. Including the controller 74 in the AVS module 50*a* may allow the controller 74 to be configured for the calibration of the solenoid valve 64. Additionally, or alternatively, including the controller 74 in the AVS module 50*a* allows the controller 74 to be close to the sensors 68, 70 which may be providing signals that could degrade if the signals needed to travel over the cable 33 to the console 28 in which the controller 74 may otherwise be installed.

The controllers 38, 74, for example, comprise a general-purpose computer, or processor, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The AVS module 50*a* and console-side connector 50*b*, for example, are compact and may be any suitable size. In some examples, the AVS module 50*a* and console-side connector 50*b* may fit into a cube of approximately 2.5 cm on all sides.

The aspiration channel 47 includes a section 47-1 coupled with an inlet port 66-1 and a section 47-2 coupled with an outlet port 62-1 (as shown in FIG. 3B). The controller 74 is configured to control the fluid connectivity in the aspiration channel 47 between the inlet port 66-1 and the outlet port 62-1 by selectively opening and closing the solenoid valve 64, responsively to a fluid metric (e.g., pressure level) in the aspiration channel 47. It should be noted that when the solenoid valve 64 is closed, the sensor 70 shown in FIG. 3B is configured to sense a fluid metric (e.g., pressure level) in the section 47-2 between the solenoid valve 64 and the console 28.

The solenoid valve 64 and its operation is now described in more detail. The solenoid valve 64 includes a valve body 78, a solenoid coil 80, and a plunger 82.

The valve body 78 includes the ports 62, the ports 66, and a valve cavity 84, with a plunger 82, movable in the valve cavity 84. The solenoid coil 80 is disposed in the valve body 78 around valve cavity 84. The plunger 82 includes a permanent magnet 88. The permanent magnet 88 may comprise all of, or only part of, the plunger 82. For example, the plunger 82 may include the permanent magnet 88 coated or covered with a material of low friction. The plunger 82 is configured to move back-and-forth along the direction of elongation 86 between a position 90 and a position 92 in the valve cavity 84 selectively controlling the fluid connectivity, by opening and closing the aspiration channel, at a location intermediate the inlet port 66-1 and the outlet port 62-1.

The plunger 82 may have any suitable size, for example, a length in the range of 3 mm to 2 cm (e.g., 6 mm) and a diameter in the range of 1 mm to 1 cm (e.g., 3 mm). The valve body 78 may include a spacer 94, as disclosed, for example, in U.S. patent application Ser. No. 17/511,166. The valve body 78 may also include one or more dampers 96 to soften impact of the plunger 82 against the valve body 78. In FIG. 3B, the upper damper 96 forms part of the spacer 94.

Figure 6:
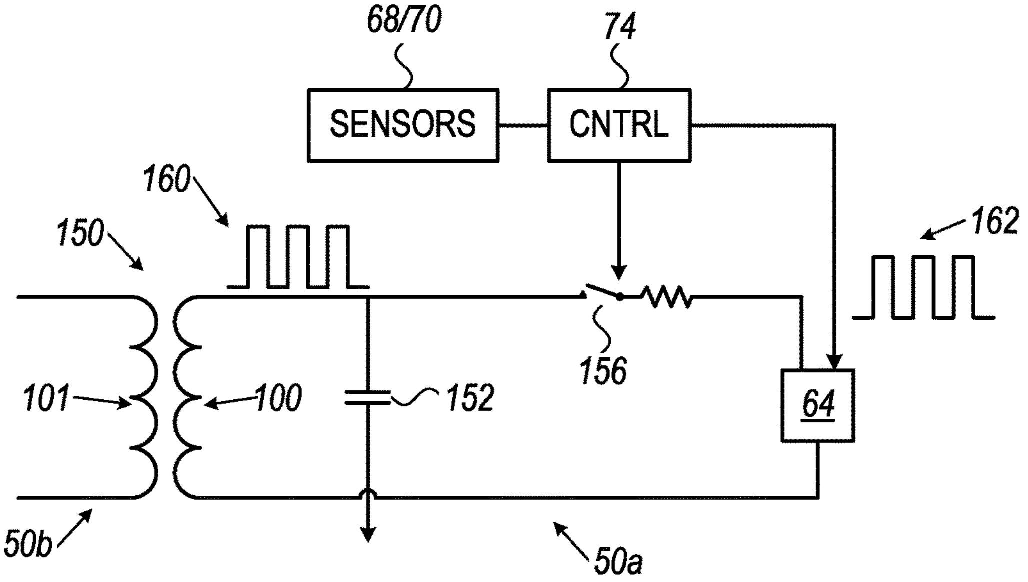
FIG. 6 is a circuit diagram of the power and/or data transfer system in accordance with an example of the present disclosure.

Turning to FIG. 6, there is shown a circuit diagram of the disclosed power and/or data transmission system 150. The AVS module 50*a* includes the coil 100, which by magnetic induction communicates with the coil 101 of the console-side connector 50*b*. In the AVS module 50*a*, the coil 100 is used for powering the module 50*a* (with electrical energy), and is also used to charge a capacitor 152, which is electrically coupled with the controller 74 (which also communicates with the sensors 68, 70) and the solenoid valve 64.

Should a vacuum surge be detected in the aspiration channel 47 in the AVS module 50*a* (47-1, 47-2 of the AVS module 50*a*) or the console-side connector 50*b*, by one or both of the sensors 68, 70, the controller 74, responds to the sensors 68, 70 having detected the vacuum surge, as the controller 74 has determined that a threshold pressure has been reached or exceeded in the aspiration channel 47. The controller 74 subsequently signals a switch 156 to close, causing the capacitor 152, to instantaneously provide additional power to the solenoid valve 64, to move to the closed state, to immediately close the aspiration channel 47. This immediate action closing the aspiration channel 47 prevents damage to the eye and its tissues.

The mated (coupled) magnetic coils 100, 101 of the AVS module 50*a* and console-side connector 50*b* provide a power scheme that alternates between providing pulses of power 160, 162 for charging the capacitor 152 and activating the AVS coil 100 with pulses. By using short pulses delivered over a fraction of a millisecond, the threshold of power, typically defined over 1 msec, may be exceeded, in order to provide a rapid charge to the capacitor 152. The rapidly charged capacitor 152 can instantaneously power the solenoid valve 64, for example, to instantly close in response to a pressure surge on the aspiration channel 47.

EXAMPLES

Example 1

A system for transferring energy and/or data between a console (28) and a medical tool (12), comprising: a first connector (50*b*) comprising at least one first coil (101); a second connector (50*a*) comprising: at least one second coil (100); and, a vacuum surge protection system (51) comprising a valve (64), the valve (64) configured to be activated by the energy transferred to the at least one second coil (100) for opening and closing a portion of an aspiration channel (47) extending through the vacuum surge protection system (51), the aspiration channel (47) in communication with at least the console (28) and the medical tool (12). The first connector (50*b*) is configured to couple with the console (28) and the second connector (50*a*), and the second connector (50*a*) is configured to couple with the medical tool (12), wherein the at least one first coil (101) and the at least one second coil (100) are configured to transfer the energy and/or data between the first connector (50*b*) and the second connector (50*a*) by magnetic induction. The system also comprises a separator (104), on either the first connector (50*b*) or the second connector (50*a*), such that when the first connector (50*b*) is coupled with the second connector (50*a*), the separator (104) is positioned between the at least one first coil (101) and the at least one second coil (100).

Example 2

The system of Example 1, wherein first connector (50*b*) is configured to couple with the second connector (50*a*) such that the at least one first coil (101) and the at least one second coil (100) are substantially aligned.

Example 3

The system of Example 1 or Example 2, wherein the at least one first coil (101) includes one coil (101), and the at least one second coil (100) includes one coil (100).

Example 4

The system of any of Example 1 to Example 3, wherein the separator (104) comprises an electrically insulating material.

Example 5

The system of any of Example 1 to Example 4, wherein the second connector (50*a*) includes the separator (104).

Example 6

The system of any of Example 1 to Example 5, wherein the medical tool (12) comprises a phacoemulsification handpiece (12).

Example 7

The system of any of Example 1 to Example 6, further comprising: an irrigation channel (45) extending through the first connector (50*b*) and the second connector (50*a*) and in communication with the console (28) and the medical tool (12); and the aspiration channel (47) extending through the first connector (50*b*).

Example 8

The system of any of Example 1 to Example 7, wherein the vacuum surge protection system (51) further comprises: a pressure sensor (70) in communication with the aspiration channel (47); and, a controller (74) in communication with the pressure sensor (70), wherein the controller (74) is configured to activate the valve (64) to close the portion of the aspiration channel (47) when the pressure in the aspiration channel (47), as detected by the pressure sensor (70), reaches a threshold pressure.

Example 9

A method for transferring energy and/or data between a console (28) and a medical tool (12), comprising: providing a system comprising: a first connector (50*b*) comprising at least one first coil (101); a second connector (50*a*) comprising: at least one second coil (100); and, a vacuum surge protection system (51) comprising a valve (64), the valve (64) configured to be activated by the energy transferred to the at least one second coil (100) for opening and closing a portion of an aspiration channel (47) extending through the vacuum surge protection system (51), the aspiration channel (47) in communication with at least the console (28) and the medical tool (12). The first connector (50*b*) couples with the second connector (50*a*) to transfer energy and/or data between the at least one first coil (101) and the at least one second coil (100).

Example 10

The method of Example 9, wherein the transfer of the energy and/or the data between the at least one first coil (101) and the at least one second coil (100) is by magnetic induction.

Example 11

The method of Example 9 or Example 10, wherein the coupling the first connector (50*b*) with the second connector (50*a*) comprises orienting the first connector (50*b*) with the second connector (50*a*) such that the at least one first coil (101) is substantially aligned with the at least one second coil (100) to facilitate energy and/or data transfer between the at least one first coil (101) and the at least one second coil (100).

Example 12

The method of any of Example 9 to Example 11, wherein the transfer of energy and/or data between the at least one first coil (101) and the at least one second coil (100), is from the at least one first coil (101) to the at least one second coil (100).

Example 13

The method of any of Example 9 to Example 12, wherein the medical tool (12) includes a phacoemulsification handpiece (12) for communication with the second connector (50*a*), and subsequent to the coupling of the first connector (50*b*) with the second connector (50*a*), performing a phacoemulsification procedure in an eye (20) of a subject (19).

Example 14

An anti-vacuum surge (AVS) module (50*a*) for communication with a medical tool (12), the AVS module (50*a*) comprising: at least one coil (100) for receiving energy and/or data transferred from at least one external coil (101) of a connector (50*b*) by magnetic induction, when the connector (50*b*) couples with the AVS module (50*a*) such that the at least one coil (100) and the at least one external coil (101) are at least substantially aligned; an irrigation channel (45) for communicating with an irrigation channel (43) of the medical tool (12); an aspiration channel (47) for communication with an aspiration channel (53) of the medical tool (12), and, a valve (64) configured to be activated by the energy transferred to the at least one coil (100) for opening and closing the aspiration channel (47) of the AVS module (50*a*); and, a separator (104) for electrically insulating the at least one coil (100) from the at least one external coil (101) when the AVS module (50*a*) is coupled with the connector (50*b*).

Example 15

The AVS module of Example 14, wherein the at least one coil (100) includes one coil (100).

Example 16

The AVS module of Example 14 or Example 15, wherein the separator (104) comprises an electrically insulating material.

Example 17

The AVS module of any one of Example 14 to Example 16, further comprising: a pressure sensor (70) in communication with the aspiration channel (47); and, a controller (74) in communication with the pressure sensor (70), wherein the controller (70) is configured to activate the valve (64) to close the aspiration channel (47) when the pressure in the aspiration channel (47), as detected by the pressure sensor (70), reaches a threshold pressure.

Although the examples described herein mainly address connectors to transfer energy and/or data between them, the methods and systems described herein can also be used in other applications, such as in other power and/or data transfers where magnetic energy is used to make the transfer.

It will thus be appreciated that the examples described above do not limit the present disclosure to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for transferring energy between a console and a medical tool, the system comprising:

a first connector comprising at least one first coil;

a second connector comprising:

at least one second coil; and a vacuum surge protection system comprising:

a valve, the valve configured to be activated by the energy transferred to the at least one second coil for opening and closing a portion of an aspiration channel extending through the vacuum surge protection system, the aspiration channel in communication with at least the console and the medical tool; and an energy-storage capacitor electrically coupled with the at least one second coil and the valve, the energy-storage capacitor configured to be charged by the energy transferred to the at least one second coil and configured to supply power to actuate the valve, wherein the first connector is configured to couple with the console and the second connector and the second connector is configured to couple with the medical tool, wherein the at least one first coil and the at least one second coil are configured to transfer the energy between the first connector and the second connector by magnetic induction; and a separator, on either the first connector or the second connector, such that when the first connector is coupled with the second connector, the separator is positioned between the at least one first coil and the at least one second coil, wherein the separator defines an aperture through which the aspiration channel extends.

2. The system of claim 1, wherein the first connector is configured to couple with the second connector such that the at least one first coil and the at least one second coil are substantially aligned.

3. The system of claim 1, wherein the separator comprises an electrically insulating material.

4. The system of claim 1, wherein the second connector includes the separator.

5. The system of claim 1, wherein the medical tool comprises a phacoemulsification handpiece.

6. The system of claim 1, further comprising:

an irrigation channel extending through the first connector and the second connector and in communication with the console and the medical tool; and the aspiration channel extending through the first connector.

7. The system of claim 1, wherein the vacuum surge protection system further comprises:

a pressure sensor in communication with the aspiration channel; and a controller in communication with the pressure sensor, wherein the controller is configured to activate the valve to close the portion of the aspiration channel when the pressure in the aspiration channel, as detected by the pressure sensor, reaches a threshold pressure.

8. The system of claim 7, further comprising a switch electrically coupled between the energy-storage capacitor and the valve, wherein the controller is configured to, when the pressure in the aspiration channel reaches the threshold pressure, close the switch to cause the energy-storage capacitor to discharge and actuate the valve to close the portion of the aspiration channel.

9. The system of claim 1, wherein the at least one first coil and the at least one second coil are further configured to transfer data between the first connector and the second connector.

10. The system of claim 1, further comprising an electrically insulating layer, on either the first connector or the second connector, such that when the first connector is coupled with the second connector, the electrically insulating layer is positioned between the at least one first coil and the at least one second coil.

11. The system of claim 10, wherein the first connector includes the electrically insulating layer.

12. The system of claim 1, wherein the energy transferred by magnetic induction to the at least one second coil is delivered as a plurality of short pulses, to charge the energy-storage capacitor, wherein each pulse is delivered over a fraction of a millisecond.

13. A method for transferring energy between a console and a medical tool, the method comprising:

providing a system comprising:

a first connector comprising at least one first coil; and a second connector comprising:

(i) at least one second coil; and (ii) a vacuum surge protection system comprising:

a valve, the valve configured to be activated by the energy transferred to the at least one second coil for opening and closing a portion of an aspiration channel extending through the vacuum surge protection system, the aspiration channel in communication with at least the console and the medical tool; and an energy-storage capacitor electrically coupled with the at least one second coil and the valve, the energy-storage capacitor configured to be charged by the energy transferred to the at least one second coil and configured to supply power to actuate the valve, and coupling the first connector with the second connector to transfer energy between the at least one first coil and the at least one second coil, charging the energy-storage capacitor via the energy transferred to the at least one second coil, and actuating the valve using power supplied by the energy-storage capacitor.

14. The method of claim 13, wherein the transfer of the energy between the at least one first coil and the at least one second coil is by magnetic induction.

15. The method of claim 14, wherein the coupling the first connector with the second connector comprises orienting the first connector with the second connector such that the at least one first coil is substantially aligned with the at least one second coil to facilitate energy transfer between the at least one first coil and the at least one second coil.

16. The method of claim 13, wherein the transfer of the energy between the at least one first coil and the at least one second coil, is from the at least one first coil to the at least one second coil.

17. The method of claim 13, wherein the medical tool includes a phacoemulsification handpiece for communication with the second connector, and subsequent to the coupling of the first connector with the second connector, performing a phacoemulsification procedure in an eye of a subject.

18. The method of claim 13, wherein the coupling between the first connector with the second connector transfers data between the at least one first coil and the at least one second coil.

19. The method of claim 13, wherein charging the energy-storage capacitor comprises delivering the energy transferred to the at least one second coil as a plurality of short pulses, each pulse having a duration of a fraction of a millisecond.

20. The method of claim 13, wherein the system further comprises a switch electrically coupled between the energy-storage capacitor and the valve, the method further comprising:

detecting that a pressure in the aspiration channel has reached a threshold pressure; and responsive to detecting that the pressure has reached the threshold pressure, closing the switch to discharge the energy-storage capacitor and actuate the valve to close the portion of the aspiration channel.

* * * * *